United States Patent
Xalter et al.

(10) Patent No.: US 8,771,561 B2
(45) Date of Patent: Jul. 8, 2014

(54) AMINOGUANIDINEPHENYLPHOSPHINATE FLAME RETARDANT COMPOSITIONS

(75) Inventors: Rainer Xalter, Ludwigshafen (CH); Thomas Weiss, Ilvesheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/695,952

(22) PCT Filed: May 5, 2011

(86) PCT No.: PCT/EP2011/057236
§ 371 (c)(1),
(2), (4) Date: Dec. 4, 2012

(87) PCT Pub. No.: WO2011/138410
PCT Pub. Date: Nov. 10, 2011

(65) Prior Publication Data
US 2013/0105745 A1 May 2, 2013

Related U.S. Application Data

(60) Provisional application No. 61/332,214, filed on May 7, 2010.

(30) Foreign Application Priority Data

May 7, 2010 (EP) ..................................... 10162285

(51) Int. Cl.
| C09K 21/12 | (2006.01) |
| C07C 279/02 | (2006.01) |
| C07C 281/16 | (2006.01) |
| C08K 5/52 | (2006.01) |
| C08K 5/5313 | (2006.01) |
| C08K 5/00 | (2006.01) |
| C07F 9/30 | (2006.01) |

(52) U.S. Cl.
CPC ............... *C09K 21/12* (2013.01); *C07C 281/16* (2013.01); *C08K 5/5205* (2013.01); *C08K 5/5313* (2013.01); *C08K 5/0066* (2013.01); *C07F 9/304* (2013.01); *C07C 279/02* (2013.01)
USPC .................................. 252/601; 562/8; 562/11

(58) Field of Classification Search
CPC .... C09K 21/12; C07C 279/02; C07C 281/16; C08K 5/0066; C08K 5/5205; C08K 5/066
USPC .......................... 524/100; 252/601; 562/8, 11
See application file for complete search history.

(56) References Cited

U.S. PATENT DOCUMENTS

| 4,107,145 A | * | 8/1978 | Simon ........................... 528/108 |
| 4,308,197 A | * | 12/1981 | Byrd et al. ..................... 442/142 |
| 5,084,546 A | | 1/1992 | Fischer et al. |
| 5,089,559 A | * | 2/1992 | Blount ........................... 525/107 |

FOREIGN PATENT DOCUMENTS

| WO | 00/02869 A1 | 1/2000 |
| WO | 2008119693 A1 | 10/2008 |

* cited by examiner

*Primary Examiner* — Michael M Bernshteyn
(74) *Attorney, Agent, or Firm* — Tyler A. Stevenson

(57) ABSTRACT

The present invention relates to flame retardant polymer compositions which comprise aminoguanidine phenylphosphinates and mixtures with additional flame retardants. The compositions are especially useful for the manufacture of flame retardant compounds based on polyfunctional epoxides or polycondensates like polyesters, polyamides and polycarbonates.

16 Claims, No Drawings

AMINOGUANIDINEPHENYLPHOSPHINATE FLAME RETARDANT COMPOSITIONS

The invention relates to flame retardant compositions, which comprise a mixture of a salt of aminoguanidine phenylphosphinate and a polymer substrate.

Flame retardants are added to polymeric materials (synthetic or natural) to enhance the flame retardant properties of the polymers. Depending on their composition, flame retardants may act in the solid, liquid or gas phase either chemically, e.g. as a spumescent by liberation of nitrogen, and/or physically, e.g. by producing a foam coverage. Flame retardants interfere during a particular stage of the combustion process, e.g. during heating, decomposition, ignition or flame spread.

There is still a need for flame retardant compositions with improved properties that can be used in different polymer substrates. A particular need is seen in suitable flame retardant compositions for the manufacture of glass-fibre reinforced epoxy prepregs, laminates, and printed circuit boards, as well as printed wiring boards derived thereof. Of special interest for these applications are flame retardants with curing properties, as their use allows replacement of a part or all of the hardener component and generally results in better mechanical and thermal properties of the laminates produced thereof.

Increased standards with regard to safety and environmental requirements result in stricter regulations. Particularly known halogen containing flame retardants no longer match all necessary requirements. Therefore, halogen free flame retardants are preferred, particularly in view of their better performance in terms of smoke density associated with fire. Improved thermal stability and decreased delamination tendency are further benefits of halogen free flame retardant compositions.

WO 00/02869 discloses polyphosphate salts of a 1,3,5-triazine compound and its use for flame retardant compositions.

U.S. Pat. Specification No. 5,084,546 discloses flame retardant epoxy resin compositions, wherein hydroxyalkyl phosphine oxides are present as active components.

Published PCT/EP 2008/053474 discloses flame retardant epoxy resin compositions, wherein 6H-dibenz[c,e][1,2]oxaphosphorin-6-oxide is present as an active component.

It has surprisingly been found that polymers with excellent flame retardant properties are prepared in the event that aminoguanidine phenylphosphinate is added to a polymer base, particularly to a polyfunctional epoxide compound.

Moreover, the quality of the laminates, such as the laminate surface smoothness or laminate integrity, is strongly increased and their delamination tendency significantly decreased as compared to laminates containing only one of the mentioned flame retardant components.

The invention relates to a composition which comprises
a) An aminoguanidine phenylphosphinate salt of the formula

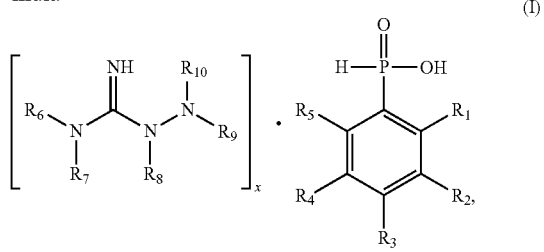

(I)

Wherein
$R_1$-$R_5$ independently of one another represent hydrogen or a substituent selected from the group consisting of $C_1$-$C_4$alkyl, hydroxy, hydroxy-$C_1$-$C_4$alkyl and $C_1$-$C_4$alkoxy;

$R_6$-$R_{11}$ independently of one another represent hydrogen or a substituent selected from the group consisting of $C_1$-$C_4$alkyl, phenyl, phenyl-$C_1$-$C_4$alkyl, ($C_1$-$C_4$alkyl)$_{1-3}$-phenyl and ($C_1$-$C_4$alkyl)$_{1-2}$ hydroxyphenyl; and x represents a number between 1.0 and 2.0;
b) A polymer substrate.

The compositions according to the invention attain the desirable V-0 rating according to UL-94 (Underwriter's Laboratories Subject 94) and other excellent ratings in related test methods especially in glass fibre reinforced compositions where conventional flame retardants tend to fail.

The compositions according to the invention are characterized by their excellent thermal and mechanical characteristics. In the context of the description of the invention, mechanical stability is defined as the ability of a laminate to withstand delamination upon heating or mechanical stress. Thermal stability is defined as the degree of resistance against decomposition upon heating. For a more precise differentiation in thermal stability of flame retardant compositions, physico-chemical methods, such as thermo-gravimetric analysis (TGA), thermo-mechanical analysis (TMA) and differential scanning calorimetry (DSC), can be used.

The flame retardant epoxy resin compositions of the present invention are especially useful for the manufacture of prepregs and laminates thereof which can be used for the preparation of printed circuit boards and printed wiring boards, or as structural segments in transportation vehicles (trains, planes, ships, automotives, etc.) and in construction applications (dry walls, floorings, beams, etc.).

A specific embodiment of the invention relates to a composition, wherein in the aminoguanidine phenylphosphinate salt (I)
$R_1$-$R_5$ represent hydrogen;
$R_6$-$R_{10}$ independently of one another represent hydrogen or $C_1$-$C_4$alkyl; and
x represents a number between 1.0 and 2.0.

A highly specific embodiment of the invention relates to a composition, wherein in the aminoguanidine phenylphosphinate salt (I)
$R_1$-$R_5$ represent hydrogen;
$R_6$-$R_{10}$ represent hydrogen; and
x represents a number between 1.0 and 2.0.

The composition, as defined above, comprises the following components:
Component a)
In the aminoguanidine phenylphosphinate salt of the formula

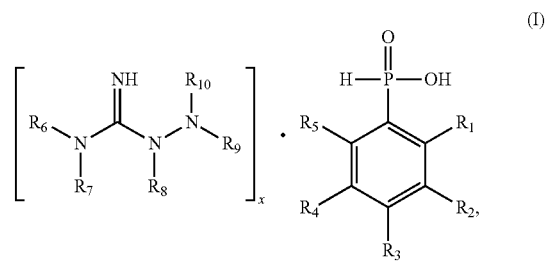

(I)

$R_1$-$R_5$ independently of one another represent hydrogen or a substituent selected from the group consisting of $C_1$-$C_4$alkyl, e.g. methyl, ethyl, n- or isopropyl, or n-, iso- or tert-butyl, hydroxy, hydroxy-$C_1$-$C_4$alkyl, e.g. hydroxymethyl or 1- or 2-hydroxyethyl and $C_1$-$C_4$alkoxy, e.g. methoxy or ethoxy;

$R_6$-$R_{10}$ independently of one another represent hydrogen or a substituent selected from the group consisting of $C_1$-$C_4$alkyl, phenyl, phenyl-$C_1$-$C_4$alkyl, e.g. benzyl or 1- or 2-phenethyl, $(C_1$-$C_4$alkyl$)_{1-3}$-phenyl, e.g. tolyl or mesityl, and $(C_1$-$C_4$alkyl$)_{1-2}$hydroxyphenyl, e.g. 4-hydroxy-3,5-di-tert-butylphenyl or 3-tert-butyl-4-hydroxy-5-methylphenyl;

And x represents a number between 1.0 and 2.0.

The aminoguanidine phenylphosphinate salt (I) is represented by the following alternative structural formulae

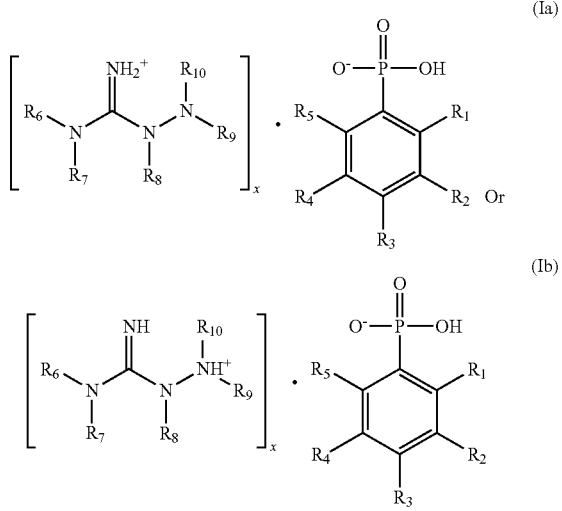

The aminoguanidine phenylphosphinate salts (I) are novel compounds and are subject matter of the present invention.

The method for preparing the aminoguanidine phenylphosphinate salts (I) is also subject matter of the present invention.

A specific embodiment of the invention relates to an aminoguanidine phenylphosphinate (I), wherein $R_1$-$R_5$ represent hydrogen;

$R_6$-$R_{10}$ independently of one another represent hydrogen or $C_1$-$C_4$alkyl; and x represents a number between 1.0 and 2.0.

A highly specific embodiment of the invention relates to a aminoguanidine phenylphosphinate (I), wherein $R_1$-$R_5$ represent hydrogen;

$R_6$-$R_{10}$ independently of one another represent hydrogen; and x represents a number between 1.0 and 2.0.

These compounds are obtainable by known methods, e.g. acid-base reaction of equivalent amounts corresponding to x of phenylphosphinic acid of the formula

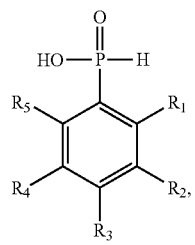

Wherein $R_1$-$R_5$ are as defined above;

With an aminoguanidine derivative of the formula

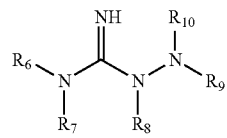

Or a salt thereof, e.g. the carbonate salt, wherein $R_6$-$R_{10}$ are as defined above.

According to a preferred embodiment, aminoguanidine phenylphosphinates are prepared from aminoguanidine hydrogencarbonate and phenylphosphinic acid, for example by addition of both components as hot aqueous solutions, followed by subsequent crystallization, filtration, drying, and milling.

A particularly preferred embodiment of the invention relates to compositions, particularly flame retardant compositions, wherein the aminoguanidine phenylphosphinate salt of the formula

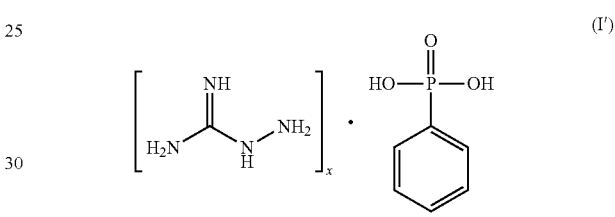

is present.

In the aminoguanidine phenylphosphinate salt (I') as defined above, the molar ratio of the phenylphosphinic acid and the aminoguanidine base is between 1:1 and 2:1, corresponding to x being between 1.0 and 2.0.

Component a) is preferably contained in the flame retardant compositions according to the invention in an amount from 0.1-45.0 wt. %, preferably 0.1-30.0 wt. %, based on the weight of the polymer substrate component b).

Component b)

The term polymer substrate comprises within its scope thermoplastic polymers or thermosets.

A list of suitable thermoplastic polymers is given below:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be cross linked), for example high density polymethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE). Polyolefins, i.e. the polymers of monoolefins exemplified in the preceding paragraph, preferably polyethylene and polypropylene, can be prepared by different and especially by the following methods:
   a) Radical polymerisation (normally under high pressure and at elevated temperature).
   b) Catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, and amine or silyl ether groups. These catalyst systems are usually termed Phillips, Standard Oil Indiana, Ziegler-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch;

The homopolymers and copolymers mentioned above may have a stereo structure including syndiotactic, isotactic, hemi-isotactic or atactic; where atactic polymers are preferred. Stereo block polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyl toluene, all isomers of ethyl styrene, propyl styrene, vinyl biphenyl, vinyl naphthalene, and vinyl anthracene, and mixtures thereof. Homopolymers and copolymers may have a stereo structure including syndiotactic, isotactic, hemi-isotactic or atactic; where atactic polymers are preferred. Stereo block polymers are also included;

a) Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

b) Hydrogenated aromatic polymers derived from hydrogenation of polymers mentioned under 6), especially including polycyclohexylethylene (PCHE) prepared by hydrogenating atactic polystyrene, often referred to as polyvinylcyclohexane (PVCH).

c) Hydrogenated aromatic polymers derived from hydrogenation of polymers mentioned under 6a). Homopolymers and copolymers may have a stereo structure including syndiotactic, isotactic, hemi-isotactic or atactic; where atactic polymers are preferred. Stereo block polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulphochlorinated polyethylene, copolymers of ethylene and chlorinated ethylene, epichlorohydrin homo- and copolymers, especially polymers of halogencontaining vinyl compounds, for example polyvinyl chloride, polyvinylidene chloride, polyvinyl fluoride, polyvinylidene fluoride, as well as copolymers thereof such as ylnyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1 above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes, which contain ethylene oxide as a co-monomer; polyacetals modified with thermoplastic polyurethanes, acrylates or MBS.

14. Polyphenylene oxides and sulphides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and co-polyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or co-polyamides modified with EPDM or ABS; and polyamides condensed during processing (RIM polyamide systems).

17. Polyureas, polyimides, polyamide imides, polyether imides, polyester imides, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block co-polyether esters derived from hydroxyl-terminated polyethers; and also polyesters modified with polycarbonates or MBS.

19. Polyketones.

20. Polysulphones, polyether sulphones and polyether ketones.

21. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

22. Polycarbonates that correspond to the general formula:

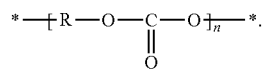

Such Polycarbonates are obtainable by interfacial processes or by melt processes (catalytic transesterification). The polycarbonate may be either branched or linear in structure and may include any functional substituents. Polycarbonate copolymers and polycarbonate blends are also within the scope of the invention. The term polycarbonate should be interpreted as inclusive of copolymers and blends with other thermoplastics. Methods for the manufacture of polycarbonates are known, for example, from U.S. Pat. Specification Nos. 3,030,331; 3,169,121; 4,130,458; 4,263,201; 4,286,083; 4,552,704; 5,210,268; and 5,606,007. A combination of two or more polycarbonates of different molecular weights may be used.

Preferred are polycarbonates obtainable by reaction of a diphenol, such as bisphenol A, with a carbonate source. Examples of suitable diphenols are:

Bisphenol A:

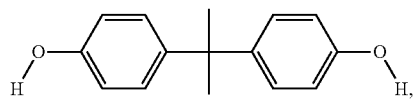

bisphenol AF:

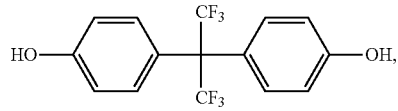

bisphenol AP:

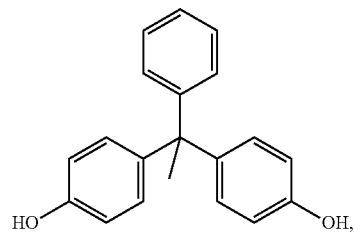

bisphenol B:

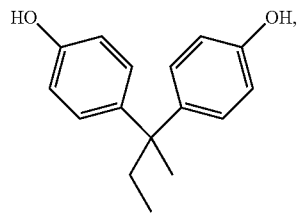

bisphenol C:

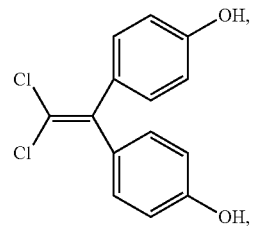

bisphenol E:

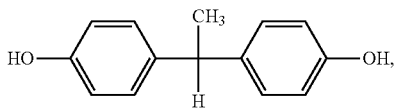

bisphenol F:

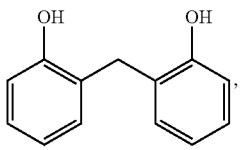

bisphenol M:

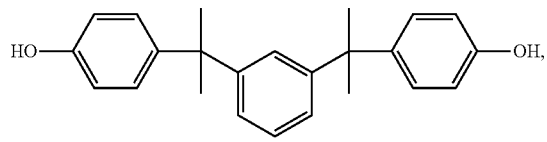

bisphenol P:

bisphenol S:

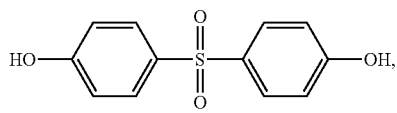

bisphenol TMC:

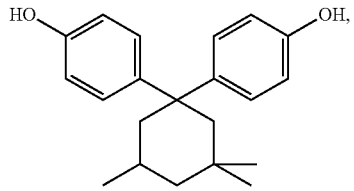

bisphenol Z:

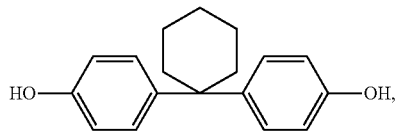

4,4'-(2-norbornylidene)bis(2,6-dichlorophenol); or fluorene-9-bisphenol

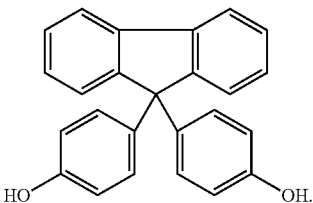 [SMILES: Oc1ccc(C2(c3ccc(O)cc3)c3ccccc3-c3ccccc32)cc1]

The carbonate source may be a carbonyl halide, a carbonate ester or a haloformate. Suitable carbonate halides are phosgene or carbonylbromide. Suitable carbonate esters are dialkylcarbonates, such as dimethyl- or diethylcarbonate, diphenyl carbonate, phenyl-alkylphenylcarbonate, such as phenyl-tolylcarbonate, dialkylcarbonates, such as dimethyl- or diethylcarbonate, di-(halophenyl)carbonates, such as di-(chlorophenyl)carbonate, di-(bromophenyl)carbonate, di-(trichlorophenyl)carbonate or di-(trichloroheny)arbonate, di-(alkylphenyl)carbonates, such as di-tolylcarbonate, naphthylcarbonate, dichloronaphthylcarbonate and others.

The polymer substrate mentioned above, which comprises polycarbonates or polycarbonate blends is a polycarbonate-copolymer, wherein isophthalate/terephthalate-resorcinol segments are present. Such polycarbonates are commercially available, e.g. Lexan® SLX (General Electrics Co. USA). Other polymeric substrates of component b) may additionally contain in the form as admixtures or as copolymers a wide variety of synthetic polymers including polyolefins, polystyrenes, polyesters, polyethers, polyamides, poly(meth)acrylates, thermoplastic polyurethanes, polysulphones, polyacetals and PVC, including suitable compatibilizing agents. For example, the polymer substrate may additionally contain thermoplastic polymers selected from the group of resins consisting of polyolefins, thermoplastic polyurethanes, styrene polymers and copolymers thereof. Specific embodiments include polypropylene (PP), polyethylene (PE), polyamide (PA), polybutylene terephthalate (PBT), polyethylene terephthalate (PET), glycol-modified polycyclohexylenemethylene terephthalate (PCTG), polysulphone (PSU), polymethylmethacrylate (PMMA), thermoplastic polyurethane (TPU), acrylonitrile-butaiene-styrene (ABS), acrylonitrile-styrene-acrylic ester (ASA), acrylonitrile-ethylenepropylene-styrene (AES), styrene-maleic anhydride (SMA) or high impact polystyrene (HIPS).

According to a preferred embodiment, the term polymer substrate of component b) consists of a polyfunctional epoxide compound, wherein at least two epoxy groups of the partial formula

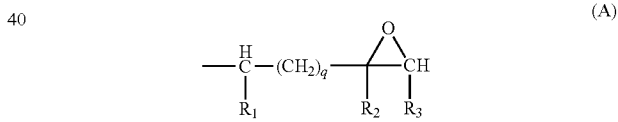

(A)

are present, which are attached directly to carbon, oxygen, nitrogen or sulphur atoms, and wherein q represents zero, $R_1$ and $R_3$ both represent hydrogen and $R_2$ represents hydrogen or methyl; or wherein q represents zero or 1, $R_1$ and $R_3$ together form the —$CH_2$—$CH_2$— or —$CH_2$—$CH_2$—$CH_2$— groups and $R_2$ represents hydrogen.

Examples of polyfunctional epoxide compounds are:
I) Polyglycidyl esters and poly(β-methylglycidyl) esters obtainable by reacting a compound having at least two carboxyl groups in the molecule with epichlorohydrin and/or glyceroldichlorohydrin and/or (β-methylepichlorohydrin. The reaction is carried out in the presence of bases.
Suitable compounds having at least two carboxyl groups in the molecule are aliphatic polycarboxylic acids, such as glutaric, adipic, pimelic, suberic, azelaic, sebacic or dimerized or trimerized linoleic acid. Cycloaliphatic polycarboxylic acids are suitable, e.g. tetrahydrophthalic, 4-methyltetrahydrophthalic, hexahydrophthalic or 4-methylhexahydrophthalic acid.
Aromatic polycarboxylic acids are suitable, such as phthalic, isophthalic, trimellitic and pyromellitic acid. Likewise suitable are carboxyl-terminated adducts of, for example, trimellitic acid and polyols such as glycerol or 2,2-bis(4-hydroxycyclohexyl)propane.

II) Polyglycidyl ethers or poly(β-methylglycidyl)ethers obtainable by reacting a compound having at least two free alcoholic hydroxyl groups and/or phenolic hydroxyl groups with a suitably substituted epichlorohydrin under alkaline conditions or in the presence of an acidic catalyst with subsequent treatment under alkaline conditions.

Ethers of this type are derived, for example, from straight-chained alcohols, such as ethyleneglycol, diethyleneglycol and higher poly(oxyethylene)glycols, propane-1,2-diol, or poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylolpropane, bistrimethylolpropane, pentaerythritol, sorbitol, and from polyepichlorohydrins.

In the alternative, they are derived, for example, from cycloaliphatic alcohols, such as 1,3- or 1,4-dihydroxycyclohexane, bis(4-hydroxycyclohexyl)methane, 2,2-bis(4-hydroxycyclohexyl)-propane or 1,1-bis(hydroxymethyl)cyclohex-3-ene, or they possess aromatic nuclei, such as N,N-bis(2-hydroxyethyl)aniline or p,p'-bis(2-hydroxyethylamino)diphenylmethane.

The epoxy compounds may also be derived from mononuclear phenols, such as resorcinol or hydroquinone; or they are based on polynuclear phenols, such as bis(4-hydroxyphenyl)methane, 2,2-bis(4-hydroxyphenyl)propane, 2,2-bis(3,5-dibromo-4-hydroxyphenyl)-propane or 4,4'-dihydroxydiphenyl sulphone, or on condensates of phenols with formaldehyde that are obtained under acidic conditions, such as phenol Novolak®.

III) Poly(N-glycidyl) compounds obtainable by dehydrochlorinating the reaction products of epichlorohydrin with amines containing at least two amino hydrogen atoms. These amines are, for example, aniline, toluidine, n-butylamine, bis(4-aminophenyl)methane, m-xylylenediamine or bis(4-methylaminophenyl)methane, and also N,N,O-triglycidyl-m-aminophenol or N,N,O-triglycidylp-aminophenol.

The poly(N-glycidyl) compounds also include N,N'-diglycidyl derivatives of cycloalkylene-ureas, such as ethylene urea or 1,3-propyleneurea, and N,N'-diglycidyl derivatives of hydantoins, such as of 5,5-dimethylhydantoin.

IV) Poly(S-glycidyl) compounds, such as di-S-glycidyl derivatives derived from dithiols, such as ethane-1,2-dithiol or bis(4-mercaptomethylphenyl)ether.

Epoxy compounds having a radical of the formula A, in which $R_1$ and $R_3$ together are —$CH_2$—$CH_2$— and n is 0 are bis(2,3-epoxycyclopentyl)ether, 2,3-epoxycyclopentyl glycidyl ether or 1,2-bis(2,3-epoxycyclopentyloxy)ethane. An example of an epoxy resin having a radical of the formula A in which $R_1$ and $R_3$ together are —$CH_2$—$CH_2$— and n is 1 is (3,4-epoxy-6-methylcyclohexyl)methyl 3',4'-epoxy-6'-methylcyclohexanecarboxylate.

Polyfunctional epoxide compounds are known. Many of them are commercially available from Huntsman Advanced Materials (brand name Araldite®). Examples of suitable polyfunctional epoxides are:

a) Liquid bisphenol A diglycidyl ethers, such as ARALDITE GY 240, ARALDITE GY 250, ARALDITE GY 260, ARALDITE GY 266, ARALDITE GY 2600, ARALDITE MY 790;

b) Solid bisphenol A diglycidyl ethers such as ARALDITE GT 6071, ARALDITE GT 7071, ARALDITE GT 7072, ARALDITE GT 6063, ARALDITE GT 7203, ARALDITE GT 6064, ARALDITE GT 7304, ARALDITE GT 7004, ARALDITE GT 6084, ARALDITE GT 1999, ARALDITE GT 7077, ARALDITE GT 6097, ARALDITE GT 7097, ARALDITE GT 7008, ARALDITE GT 6099, ARALDITE GT 6608, ARALDITE GT 6609, ARALDITE GT 6610;

c) Liquid bisphenol F diglycidyl ethers, such as ARALDITE GY 281, ARALDITE GY 282, ARALDITE PY 302, ARALDITE PY 306;

d) Solid polyglycidyl ethers of tetraphenylethane, such as CG Epoxy Resin 0163;

e) Solid and liquid polyglycidyl ethers of phenol-formaldehyde Novolak®, such as EPN 1138, EPN 1139, GY 1180, PY 307;

f) Solid and liquid polyglycidyl ethers of o-cresol-formaldehyde NOVOLAK, such as ECN 1235, ECN 1273, ECN 1280, ECN 1299;

g) Liquid glycidyl ethers of alcohols, such as Shell glycidyl ether 162, ARALDITE DY 0390, ARALDITE DY 0391;

h) Liquid glycidyl ethers of carboxylic acids, such as Shell Cardura E terephthalic ester, trimellitic ester, ARALDITE PY 284;

i) Solid heterocyclic epoxy resins (triglycidyl isocyanurate), such as ARALDITE PT 810;

k) Liquid cycloaliphatic epoxy resins, such as ARALDITE CY 179;

l) Liquid N,N,O-triglycidyl ethers of p-aminophenol, such as ARALDITE MY 0510;

m) Tetraglycidyl-4,4'-methylenebenzamine or N,N,N',N-tetraglycidyldiaminohenylmethane, such as ARALDITE MY 720, ARALDITE MY 721.

If desired, a mixture of epoxy compounds of different structure can also be employed.

Suitable polyfunctional epoxide compounds preferably comprise at least two groups of the formula

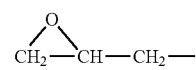

Particular preference as component is given to the following compounds of types and/or mixtures of them

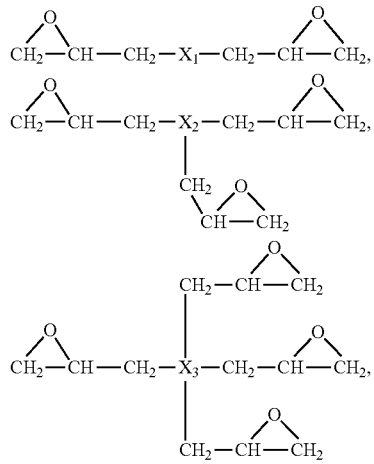

Wherein $X_1$, $X_2$ and $X_3$ are cyclohexylene, phenylene or naphthylene which can be unsubstituted or substituted and $X_1$ is additionally an unsubstituted or substituted radical of the partial formula

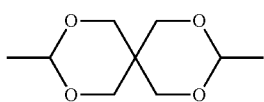

and $X_2$ is additionally an unsubstituted or substituted radical of the partial formula

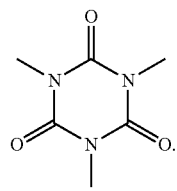

Suitable substituents for the abovementioned radicals are —O—, —S—, —C(=O)—, —C(=O)—O—, —S(=O)—, —S(O$_2$)—, —C(CF$_3$)$_2$—, alkyl, alkylene, aryl, arylene, alkoxy, aryloxy or halogen. Identical or different substituents may be present two or more times, whereas the substituents themselves may likewise be further substituted.

An example of a suitable alkyl radical is a $C_1$-$C_{18}$alkyl radical, such as methyl, ethyl, npropyl, n-butyl, sec-butyl, tert-butyl, n-hexyl, n-octyl, 2-ethylhexyl, n-nonyl, n-decyl, nundecyl, n-dodecyl, n-tridecyl, n-tetradecyl, n-hexadecyl or n-octadecyl, and their branched isomers.

Possible alkylene and alkoxy radicals can be derived formally from the above-mentioned alkyl radicals by removing a further hydrogen atom or, respectively, by adding an oxygen atom.

Examples of suitable aryl radicals are those having 6-20 carbon atoms, such as phenylene, biphenylene or naphthylene.

Possible arylene and aryloxy radicals can be derived formally from the above-mentioned aryl radicals by removing a further hydrogen atom or, respectively, by adding an oxygen atom.

Preference is given to radicals of the following formulae: for $X_1$:

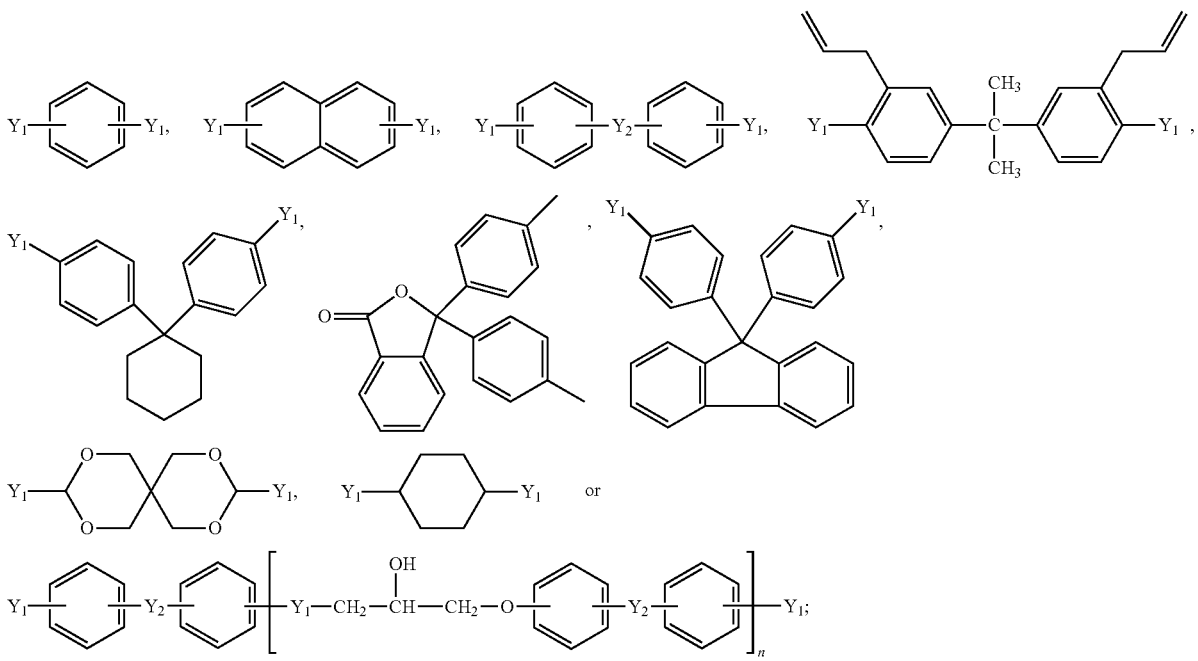

for $X_2$:

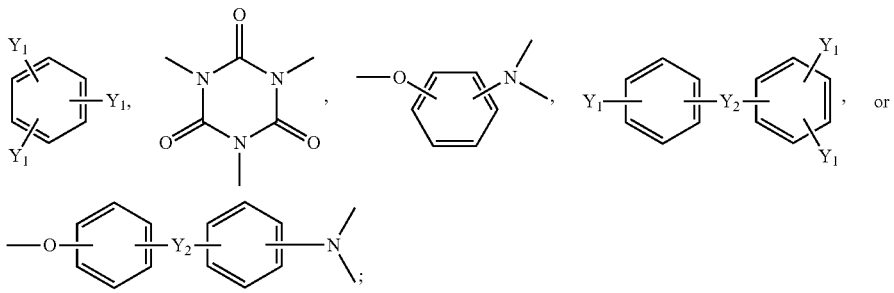

for X₃:
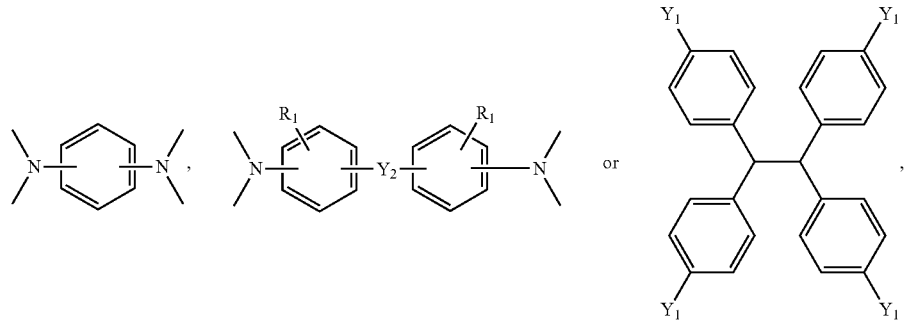
in which
Y₁ is a direct bond or the groups —O—, —S— or —C(=O)—O—;
Y₂ is a direct bond or the groups —SO₂—, —CO—, —S—, —SO—, CH₂—, —C(CH₃)₂— or —C(CF₃)₂—;
And n is 1-10.
The aromatic groups are unsubstituted or substituted one or more times by alkyl, aryl, alkoxy, aryloxy or halogen, as described in more detail above.
Particular preference is given to the following compounds:
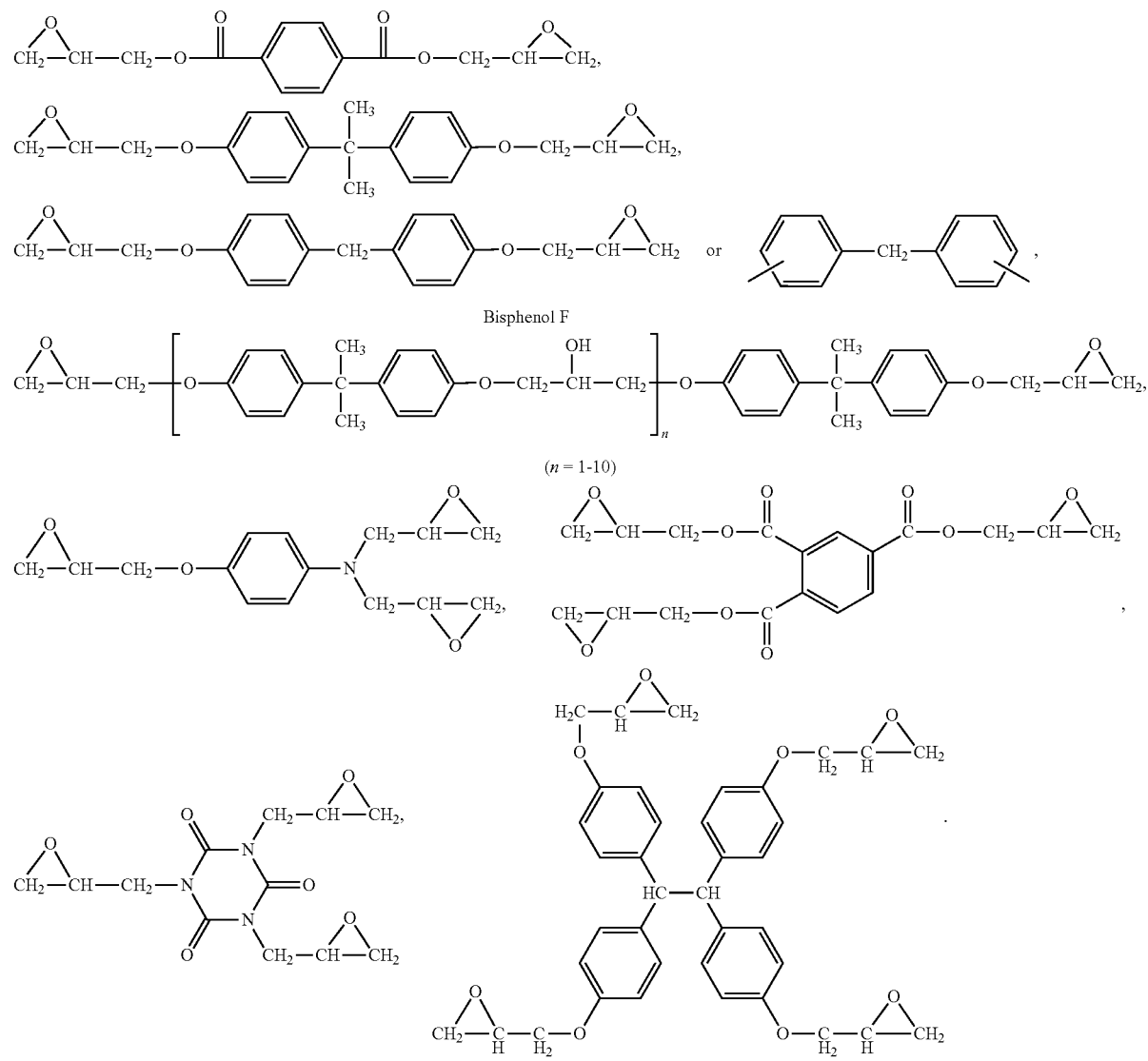

It has surprisingly been found that the guanidine phenylphosphinate (I) has curing properties. Therefore, a further embodiment of the invention relates to the preparation of well-cured laminates with excellent mechanical properties without use of any additional hardener components.

Therefore, the presence of a conventional hardener component is optional in the composition. A suitable hardener compound is any of the known hardeners for epoxy resins. The amine, phenolic and anhydride hardeners are particularly preferred, such as polyamines, e.g. ethylenediamine, diethylenetriamine, triethylenetetramine, hexamethylenediamine, methanediamine, N-aminoethyl piperazine, diaminodiphenylmethane [DDM], alkyl-substituted derivatives of DDM, isophoronediamine [IPD], diaminodiphenylsulphone [DDS], 4,4-methylenedianiline [MDA], or m-phenylenediamine [MPDA]), polyamides, alkyl/alkenyl imidazoles, dicyanodiamide [DICY], 1,6-hexamethylene-bis-cyanoguanidine, phenolic hardeners such as phenol novolac and cresol novolac, or acid anhydrides, e.g. dodecenylsuccinic acid anhydride, hexahydrophthalic acid anhydride, tetrahydrophthalic acid anhydride, phthalic acid anhydride, pyromellitic acid anhydride, styrene-maleic acid anhydride copolymers, and derivatives thereof.

A preferred embodiment of the invention relates to a composition, which comprises as component b) a polyfunctional epoxide compound and a hardener compound that contains at least two amino groups, such as dicyandiamide.

A particularly preferred embodiment of the invention relates to a composition, which comprises a) About 0.05-30.0 wt. % of aminoguanidine phenylphosphinate salt (I);

b) About 30.0-95.0 wt % of a polyfunctional epoxide compound; and 0-60.0 wt % of a hardener compound.

Additional Components

The instant invention further pertains to a composition, which comprises, in addition to the components a) and b), as defined above, as optional components, additional flame retardants and further additives selected from the group consisting of so-called anti-dripping agents and polymer stabilizers.

According to a preferred embodiment the composition contains additional flame retardants selected from the group consisting of phosphorus containing flame retardants, nitrogen containing flame retardants, halogenated flame retardants and inorganic flame retardants.

According to a preferred embodiment, the aminoguanidine phenylphosphinate salt (I) is combined in the flame retardant compositions of the invention with the phosphorus containing flame-retardant oxaphosphorinoxide or a derivative thereof, as represented by the formula (II)

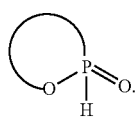

In the oxaphosphorinoxide (II) the phosphorous atom and one oxygen atom are part of a cyclic structure, particularly a five or six membered ring, and at least one group of the partial formula

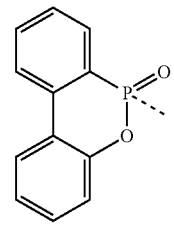

(A)

is present.

According to a preferred embodiment, the oxaphosphorinoxide (II) is represented by the following structural formula:

(IIa)

which can be named as 6H-dibenz[c,e][1,2]oxaphosphorin-6-oxide, 3,4:5,6-dibenzo-2H-1,2-oxaphosphorin-2-oxide or 9,10-dihydro-9-oxa-10-phosphorylphenanthrene-10-oxide, abbreviated as DOPO (C.A. RN 35948-25-5). Such compound is commercially available from Sanko Co, Ltd. under the trade name Sanko-HCA.

Two different structural formulae may be assigned to DOPO and its hydrolysis product:

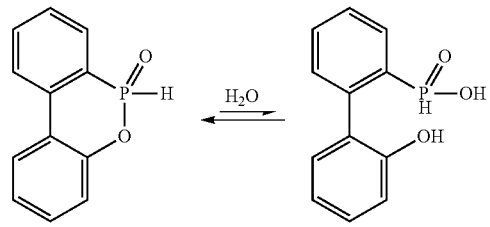

Suitable derivatives of oxaphosphorinoxide are 9,10-dihydro-9-oxa-10-phosphorylphenanthrene-10-oxide (DOPO), salts of DOPO, such as the zinc salts

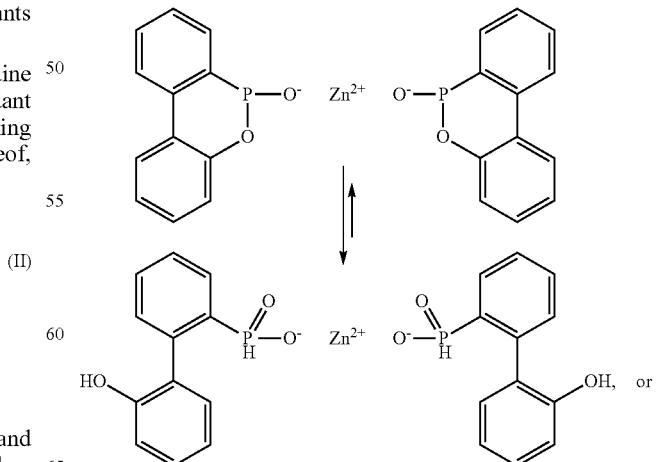

R-substituted oxaphosphorinoxides of the formula

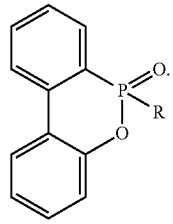 (IIb)

Wherein the phenyl groups may be substituted by additional substituents and R represents $C_1$-$C_{18}$alkyl or $C_6$-$C_{12}$ aryl, which may be substituted by further substituents.

Representative compounds (IIb) are compounds of the formula:

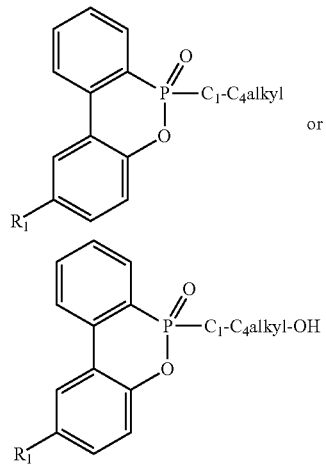

Wherein $R_1$ represents hydrogen or $C_1$-$C_4$alkyl;

Other representative compounds (IIb) are compounds, wherein R represents carboxyalkyl, carboxyalkyl which is esterified by hydroxyalkyl, or represents carboxylmidoalkyl, such as the compounds of the formulae:

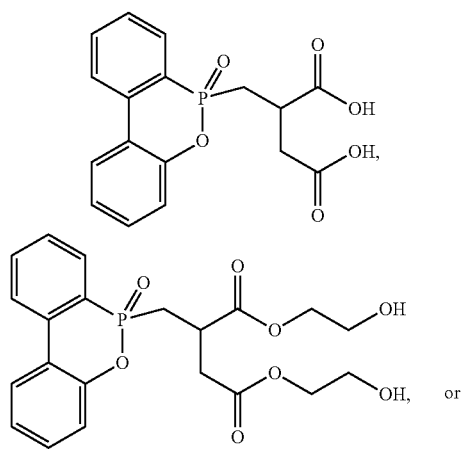

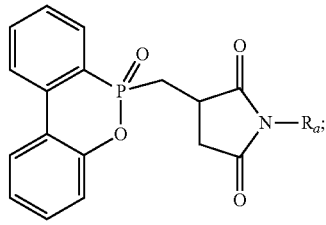

Wherein $R_a$ represents hydrogen or $C_1$-$C_{14}$alkyl; or represents alkoxyalkyl, such as the compounds of the formula:

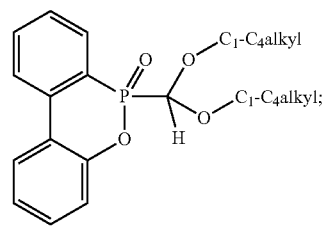

Aryl, such as the compounds of the formulae:

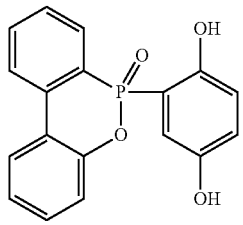

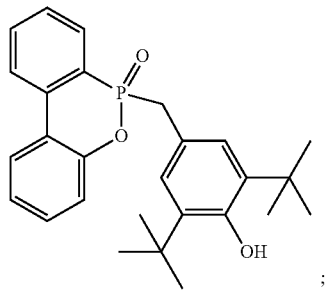

Or wherein R represents arylalkyl, such the compounds of the formulae

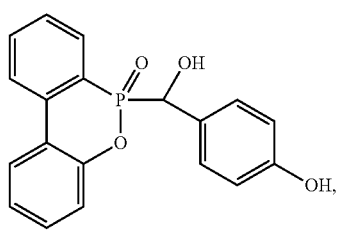

-continued

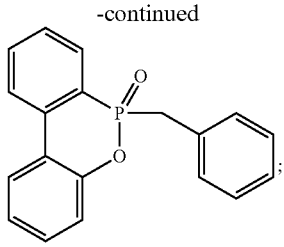

Or wherein R represents alkoxyalkyl substituted by hydroxy, such as the compound of the formula

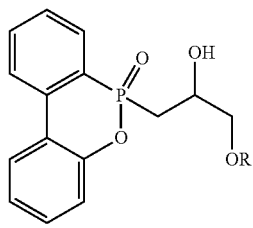

as obtained by reaction of DOPO with epoxides:

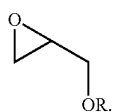

The oxaphosphorinoxides as defined above are known compounds or can be prepared by known methods. Some of them are commercially available.

According to another preferred embodiment, the aminoguanidine phenylphosphinate salt (I) is combined in the flame retardant compositions of the invention with a salt of $diC_1$-$C_4$alkylphosphinic acid, particularly the $Ca^{2+}$, $Zn^{2+}$, or $Al^{3+}$ salt, as phosphorus containing flame retardant.

The di-$C_1$-$C_4$alkylphosphinic acid has identical or different $C_1$-$C_4$alkyl groups, such as dimethyl, diethyl, ethylmethyl or methyl-n-propylphosphinic acid. Such products are known and commercially available (Exolit® OP series, Clariant).

Particularly preferred are the aluminum salts of di-$C_1$-$C_4$alkylphosphinic acid, such as dimethylphosphinic acid, diethylphosphinic acid (DEPAL) or methyl-ethylphospinic acid (MEPAL).

According to another preferred embodiment, the aminoguanidine phenylphosphinate salt (I) is combined in the flame retardant compositions of the invention with triphenylphosphine oxide as the phosphorus containing flame retardant.

According to a further embodiment of the invention, the composition comprises as optional components further flame retardants selected from the group of selected from the group consisting of phosphorus containing flame retardants, nitrogen containing flame retardants, halogenated flame retardants and inorganic flame retardants. Such additional flame retardants are known components, items of commerce or can be obtained by known methods.

Other representative phosphorus containing flame retardants, in addition to the ones defined above, are for example: Tetraphenyl resorcinol diphosphate (Fyrolflex® RDP, Akzo Nobel), resorcinol diphosphate oligomer (RDP), triphenyl phosphate, ethylenediamine diphosphate (EDAP), diethyl-N,N-bis(2-hydroxyethyl)-aminomethyl phosphonate, hydroxyalkyl esters of phosphorus acids, salts of hypophosphoric acid ($H_3PO_2$) comprising e.g. $Ca^{2+}$, $Zn^{2+}$, or $Al^{3+}$ as cations, tetrakis(hydroxymethyl)phosphonium sulphide, ammonium polyphosphate and phosphazene flame-retardants.

Nitrogen containing flame retardants are, for example, isocyanurate flame retardants, such as polyisocyanurate, esters of isocyanuric acid or isocyanurates. Representative examples are hydroxyalkyl isocyanurates, such as tris-(2-hydroxyethyl)isocyanurate, tris(hydroxymethyl)isocyanurate, tris(3-hydroxy-n-proyl)isocyanurate or triglycidyl isocyanurate.

Nitrogen containing flame-retardants include further melamine-based flame-retardants. Representative examples are: melamine cyanurate, melamine borate, melamine phosphate, melamine pyrophosphate, melamine polyphosphate, melamine ammonium polyphosphate, melamine ammonium pyrophosphate, dimelamine phosphate and dimelamine pyrophosphate.

Further examples are: benzoguanamine, tris(hydroxyethyl)isocyanurate, allantoin, glycoluril, melamine cyanurate, melamine phosphate, dimelamine phosphate, urea cyanurate, ammonium polyphosphate, a condensation product of melamine from the series melem, melam, melon and/or a higher condensed compound or a reaction product of melamine with phosphoric acid or a mixture thereof.

Representative organohalogen flame retardants are, for example:

Polybrominated diphenyl oxide (DE-60F, Great Lakes Corp.), decabromodiphenyl oxide (DBDPO; Saytex® 102E), tris[3-bromo-2,2-bis(bromomethyl)propyl]phosphate (PB 370®, FMC Corp.), tris(2,3-dibromopropyl) phosphate, tris(2,3-dichloropropyl)phosphate, chlorendic acid, tetrachlorophthalic acid, tetrabromophthalic acid, poly-β-chloroethyl triphosphonate mixture, tetrabromo-bisphenol A bis(2,3-dibromopropyl ether) (PE68), brominated epoxy resin, ethylene-bis(tetrabromophthalimide) (Saytex® BT-93), bis(hexachlorocyclopentadieno)cyclooctane (Declorane Plus®), chlorinated paraffins, octabromodiphenyl ether, hexachlorocyclopentadiene derivatives, 1,2-bis(tribromophenoxy)ethane (FF680), tetrabromo-bisphenol A (Saytex® RB100), ethylene bis(dibromo-norbornanedicarboximide) (Saytex® BN-451), bis(hexachlorocycloentadieno)cyclooctane, PTFE, tris(2,3-dibromopropyl)-isocyanurate, and ethylene-bistetrabromophthalimide.

The flame retardants mentioned above are routinely combined with an inorganic oxide synergist. Most common for this use are zinc or antimony oxides, e.g. $Sb_2O_3$ or $Sb_2O_5$. Boron compounds are suitable, too.

Representative inorganic flame retardants include, for example, aluminum trihydroxide (ATH), boehmite (AlOOH), magnesium dihydroxide (MDH), zinc borates, $CaCO_3$, (organically modified) layered silicates, (organically modified) layered double hydroxides, and mixtures thereof.

The above-mentioned additional flame retardant classes are advantageously contained in the composition of the invention in an amount from about 0.5% to about 45.0% by weight of the organic polymer substrate; for instance about 1.0% to about 40.0%; for example about 5.0% to about 35.0% by weight of the polymer or based on the total weight of the composition.

According to another embodiment, the invention relates to a composition which additionally comprises as additional component so-called anti-dripping agents.

These anti-dripping agents reduce the melt flow of the thermoplastic polymer and inhibit the formation of drops at high temperatures. Various references, such as U.S. Pat. Specification No. 4,263,201, describe the addition of anti-dripping agents to flame retardant compositions.

Suitable additives that inhibit the formation of drops at high temperatures include glass fibres, polytetrafluoroethylene (PTFE), high temperature elastomers, carbon fibres, glass spheres and the like.

The addition of polysiloxanes of different structures has been proposed in various references; cf. U.S. Pat. Specification Nos. 6,660,787, 6,727,302 or 6,730,720.

Stabilizers are preferably halogen-free and selected from the group consisting of nitroxyl stabilizers, nitrone stabilizers, amine oxide stabilizers, benzofuranone stabilizers, phosphite and phosphonite stabilizers, quinone methide stabilizers and monoacrylate esters of 2,2'-alkylidenebisphenol stabilizers.

As mentioned above, the composition according to the invention may additionally contain one or more conventional additives, for example selected from pigments, dyes, plasticizers, antioxidants, thixotropic agents, levelling assistants, basic co-stabilizers, metal passivators, metal oxides, organophosphorus compounds, further light stabilizers and mixtures thereof, especially pigments, phenolic antioxidants, calcium stearate, zinc stearate, UV absorbers of the 2-hydroxy-benzophenone, 2-(2'-hydroxyphenyl)benzotriazole and/or 2-(2-hydroxyphenyl)-1,3,5-triazine groups.

Preferred additional additives for the compositions as defined above are processing stabilizers, such as the above-mentioned phosphites and phenolic antioxidants, and light stabilizers, such as benzotriazoles. Preferred specific antioxidants include octadecyl 3-(3,5-di-tert-butyl-4-hydroxyphenyl) propionate (IRGANOX 1076), pentaerythritoltetrakis[3-(3,5-di-tert-butyl-4-hydroxyphenyl)propionate] (IRGANOX 1010), tris(3,5-di-tert-butyl-4-hydroxyphenyl)isocyanurate (IRGANOX 3114), 1,3,5-trimethyl-2,4,6-tris(3,5-di-tert-butyl-4-hydroxybenzyl)benzene (IRGANOX 1330), triethyleneglycolbis[3-(3-tert-butyl-4-hydroxy-5-methylphenyl) propionate] (IRGANOX 245), and N,N'-hexane-1,6-diyl-bis [3-(3,5-di-tert-butyl-4-hydroxyphenyl)propionamide] (IRGANOX 1098). Specific processing stabilizers include tris(2,4-di-tert-butylphenyl) phosphite (IRGAFOS 168), 3,9-bis(2,4-di-tert-butylphenoxy)-2,4,8,10-tetraoxa-3,9-diphosphaspiro[5.5]undecane (IRGAFOS 126), 2,2',2"-nitrilo[triethyl-tris(3,3',5,5'-tetra-tert-butyl-1,1'-biphenyl-2,2'-diyl)] phosphite (IRGAFOS 12), and tetrakis(2,4-di-tert-butylphenyl)-[1,1-biphenyl]-4,4'-diylbisphosphonite (IRGAFOS P-EPQ). Specific light stabilizers include 2-(2H-benzotriazole-2-yl)-4,6-bis(1-methyl-1-phenylethyl)phenol (TINUVIN 234), 2-(5-chloro(2H)-benzotriazole-2-yl)-4-(methyl)-6-(tert-butyl)phenol (TINUVIN 326), 2-(2H-benzotriazole-2-yl)-4-(1,1,3,3-tetramethylbutyl)phenol (TINUVIN 329), 2-(2H-benzotriazole-2-yl)-4-(tert-butyl)-6-(sec-butyl)phenol (TINUVIN 350), 2,2'-methylenebis(6-(2H-benzotriazol-2-yl)-4-(1,1,3,3-tetramethylbutyl)phenol) (TINUVIN 360), and 2-(4,6-diphenyl-1,3,5-triazin-2-yl)-5-Rhexyl)oxyl-phenol (TINUVIN 1577), 2-(2'-hydroxy-5'-methylphenyl)benzotriazole (TINUVIN P), 2-hydroxy-4-(octyloxy)benzophenone (CHIMASSORB 81), 1,3-bis-[(2'-cyano-3',3'-diphenylacryloyl)oxy]-2,2-bis-{[(2'-cyano-3', 3"-diphenylacryloyl)oxy]methyl}-propane (UVINUL 3030, BASF), ethyl-2-cyano-3,3-diphenylacrylate (UVINUL 3035, BASF), and (2-ethylhexyl)-2-cyano-3,3-diphenylacrylate (UVINUL 3039, BASF).

The additives mentioned above are preferably contained in an amount of 0.01 to 10.0%, especially 0.05 to 5.0%, relative to the weight of the polymer substrate b).

The incorporation of the components defined above into the polymer component is carried out by known methods such as dry blending in the form of a powder, or wet mixing in the form of solutions, dispersions or suspensions for example in an inert solvent, water or oil. The additive components a) and b) and optional further additives may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc.), e.g. as a dry mixture or powder, or as a solution or dispersion or suspension or melt.

The addition of the additive components to the polymer substrate can be carried out in customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contra-rotating and co-rotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion, Vol.* 1 Grundlagen, Editors F. Hensen, W. Knappe, H. Potente, 1989, pp. 3-7, ISBN:3-446-14339-4 (*Vol.* 2 *Extrusionsanlagen* 1986, ISBN 3-446-14329-7).

For example, the screw length is 1-60 screw diameters, preferably 35-48 screw diameters. The rotational speed of the screw is preferably 10-600 rotations per minute (rpm), preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components is added, these can be premixed or added individually.

The additive components a) and optional further additives can also be sprayed onto the polymer substrate b). The additive mixture dilutes other additives, for example the conventional additives indicated above, or their melts so that they can be sprayed also together with these additives onto the polymer substrate. Addition by spraying during the deactivation of the polymerisation catalysts is particularly advantageous; in this case, the steam evolved may be used for deactivation of the catalyst. In the case of spherically polymerised polyolefins it may, for example, be advantageous to apply the additives of the invention, optionally together with other additives, by spraying.

The additive components a) and optional further additives can also be added to the polymer in the form of a master batch ("concentrate") which contains the components in a concentration of, for example, about 1.0% to about 40.0% and preferably 2.0% to about 20.0% by weight incorporated in a polymer. The polymer is not necessarily of identical structure than the polymer where the additives are added finally. In such operations, the polymer can be used in the form of powder, granules, solutions, and suspensions or in the form of lattices.

Incorporation can take place prior to or during the shaping operation. The materials containing the additives of the invention described herein preferably are used for the production of molded articles, for example roto-molded articles, injection molded articles, profiles and the like, and especially a fibre, spun melt non-woven, film or foam.

A preferred embodiment of the invention furthermore relates to a process for the production of an epoxy resin composition having flame retardant properties which comprises mixing at least one polyfunctional epoxide compound b), an effective amount of at least one melamine phosphinate salt (I), optionally combined with oxaphosphorinoxide or a derivative thereof, and a hardener compound, optionally in the presence of a suitable accelerator, such as methyl imidazole.

The process is carried out in a known manner by analogous methods, such as the ones described in U.S. Pat. Specification No. 5,084,546.

A further embodiment of the invention relates to a mixture, which comprises

An aminoguanidine phenylphosphinate salt (I), wherein
$R_1$-$R_5$ independently of one another represent hydrogen or a substituent selected from the group consisting of $C_1$-$C_4$alkyl, hydroxy, hydroxy-$C_1$-$C_4$alkyl and $C_1$-$C_4$alkoxy; and
$R_6$-$R_{10}$ independently of one another represent hydrogen or a substituent selected from the group consisting of $C_1$-$C_4$alkyl, phenyl, phenyl-$C_1$-$C_4$alkyl, ($C_1$-$C_4$ alkyl)$_{1-3}$-phenyl and ($C_1$-$C_4$alkyl)$_{1-2}$hydroxyphenyl;

In combination with an additional flame retardant, particularly a flame retardant selected from the group consisting of phosphorus containing flame retardants, nitrogen containing flame retardants, halogenated flame retardants and inorganic flame retardants.

The components (I) and (II) are admixed to the polyfunctional epoxide compound in concentrations of 0.05-30.0 wt. %, preferably 0.1-20.0 wt. % for component a) and 0.5-40.0 wt. %, preferably 1.0-25 wt. % for component b).

The preferred ratio of components a):b) is in the range 10:1-1:10, preferably 5:1-1:5.

A further embodiment of the invention relates to a process for imparting flame retardancy to a polymer substrate, which process comprises adding to a polymer substrate the above defined aminoguanidine phenylphosphinate salt (I).

A preferred embodiment of the invention relates to a process for imparting flame retardancy to a hardened polyfunctional epoxide composition, which process comprises adding the above-defined flame retardants and flame retardant mixtures and a hardener compound to the polyfunctional epoxide.

Typical applications for such flame retarded epoxy compositions include, but are not limited to, epoxy-glass cloth laminate composites used e.g. for the manufacture of printed circuit boards (PCB's), or used as structural elements in transportation vehicles (trains, planes, ships, automotives, etc.) and in construction applications (dry walls, floorings, beams, etc.).

A further embodiment of the invention relates to a process for imparting flame retardancy to a any polymer substrate, which process comprises adding component a) to the polymer substrate b).

The following examples illustrate the invention, but are not meant to limit the scope thereof in any manner:

Components and Reagents

Aminoguanidine phenylphosphinate: 380.2 g (2.68 mol) phenylphosphinic acid (Aldrich, Germany) are dissolved at room temperature in 1.25 lethanol, and the solution is heated to 65° C. 364.2 g (2.68 mol) aminoguanidine hydrogencarbonate (Aldrich, Germany) is added over a period of 35 min. in small portions after each cessation of carbon dioxide evolution. After completing the addition, the mixture is stirred for another 90 min. at 65° C. The clear, colourless solution is concentrated to dryness in the rotary evaporator. The solid residue formed is dried at 60° C. over night in an air circulation drying oven and then for 17 h in a vacuum oven at 130° C. 578 g (2.68 mol, 99.8%) of the above product are obtained as a colourless, crystalline solid.
$C_7H_{13}N_4O_2P$ ($M_w$: 216.17); %-P: 14.2% found (14.3% calc.), M.p.: 70° C., TGA (onset): 259° C.

o-Cresol NOVOLAC epoxy resin: Araldite® ECN 1280, Huntsman Advanced Materials, Basel, Switzerland;

Hardener: Dicyandiamide (DICY), accelerator: 2-methylimidazole, both from Aldrich, Germany;

Solvents: Methoxy-2-propanol and dimethylformamide, Merck Eurolab, Germany;

Aluminium trihydroxide (ATH): Martinal®OL 104 WE, Martinswerk, Germany;

Melamine polyphosphate: Melapur® 200, BASF Schweiz AG, Switzerland;

Glass cloth: Type 7628, P-D Interglas Technologies AG, Germany.

Test Methods to Assess Flame Retardancy

UL 94 test for "*Flammability of Plastic Materials for Parts in Devices and Appliances*", 5$^{th}$ edition, Oct. 29, 1996. Ratings according to the UL 94 V test are compiled in the following table (time periods are indicated for one specimen):

| Rating | After flame time [sec] | Burning drips | Burn to clamp |
| --- | --- | --- | --- |
| V-0 | <10 | No | No |
| V-1 | <30 | No | No |
| V-2 | <30 | Yes | No |
| nc | <30 | | Yes |
| nc | >30 | | No | nc: no classification

Standard Procedure

A resin formulation is prepared using different amounts of Araldite® ECN 1280 resin in 37.5 parts methoxy-2-propanol at 95° C. 0.04 parts of 2-methylimidazole and the specific quantity of aminoguanidine phenylphosphinate according to Table 1. After each mixing at 95° C. for 15 min. clear solutions are obtained. DICY (solution in solvent mixture of DMF and methoxy-2-propanol) in the amounts specified in Table is added.

The composition is coated onto a piece of glass cloth and heated to 170° C. for about 1-3 min in a forced draft oven. The time in the forced draft oven is varied slightly from sample to sample in order to control resin flow of the final laminate. The fibre material, now in the shape of a non-tacky prepreg, is cut into 7 strips (~180×180 mm) which are stacked upon each other in a distance holder, to assure the manufacture of laminates with uniform thickness of 1.5 mm. The strips are covered with two Teflon® plates of 1 mm thickness on the upper and the lower side of the prepreg stack. The stack is placed on a hot press, and the stacked prepregs are subjected to elevated temperature and pressure according to the following general schedule:

1 minute at 170° C. with no pressure applied,
120 minutes at 170° C. with pressure of about 3 bar applied.

The resulting laminate is then removed from the press, cooled to ambient temperature, and separated from the distance holder and Teflon® plates. The laminate is cut into pieces of ~150×150 mm by cutting off the edges with varying amounts of resin, weighed, its thickness measured, and its percent resin content determined. The laminate is cut into five strips (125×13.0 mm) which are conditioned for 24 h at 23° C. and 50% relative humidity and subsequently tested in the previously mentioned UL-94 flammability test. The data obtained in this test are presented in the Table.

TABLE

| Composition | FR Additives [wt.-%] | DICY [wt.-%] | Resin [wt.-%] | UL94 Rating [1.5 mm] | Total Burning time [sec] |
|---|---|---|---|---|---|
| 1 | w/o | 7.51 | 37.2 | n.c. | 215 |
| 2 | w/o | 0.00 | No curing of resin | | |
| 3 | 35% ATH | 4.88 | 48.1 | V-1 | 77 |
| 4 | 15.8% Compound 1[1)] | 0.00 | 35.6 | V-1 | 97 |
| 5 | 19.0% Compound 1[1)] | 0.00 | 35.6 | V-1 | 71 |
| 6 | 23.8% Compound 1[1)] | 0.00 | 35.6 | V-0 | 45 |
| 7 | 11.0% Compound 1[1)] + 5.0% MPP | 1.91 | 41.9 | V-1 | 125 |
| 8 | 8.0% Compound 1[1)] + 35.0% ATH | 1.08 | 47.9 | V-0 | 31 |
| 9 | 5.0% Compound 1[1)] + 3.0% MPP + 35% ATH | 2.28 | 49.9 | V-1 | 39 |

[1)]Aminoguanidine phenylphosphinate

The data presented in the Table demonstrate that the resin compositions, as claimed, wherein the representative Test Compound 1 is present, exhibit improved flame retardant properties as compared with resin compositions containing other flame retardant component (ATH). This is demonstrated for resin compositions that contain Test Compound I, either alone (Test Compositions 4-6) or in combination with other flame retardant (Test Compositions 7-9).

In addition, the results of Compositions 4-6 show that aminoguanidine phenylphosphinates (I) have curing properties. In contrast to Referential Composition 2 where no curing was achieved under the manufacturing conditions employed, Compositions 4-6 exemplify the preparation of well-cured laminates with excellent mechanical properties without use of any additional hardener components.

The invention claimed is:

1. A composition which comprises
a) an aminoguanidine phenylphosphinate salt of formula (I)

$$\left[ \begin{array}{c} NH \\ R_6 \diagdown \underset{R_7}{N} \diagdown \underset{R_8}{\overset{|}{C}} \diagdown \underset{R_9}{\overset{|}{N}} \diagdown R_{10} \end{array} \right]_x \cdot \begin{array}{c} O \\ \| \\ H-P-OH \\ | \\ \text{(phenyl with } R_1\text{-}R_5) \end{array} \tag{I}$$

wherein
$R_1$-$R_5$ independently of one another represent hydrogen or a substituent selected from the group consisting of $C_1$-$C_4$alkyl, hydroxy, hydroxy-$C_1$-$C_4$alkyl and $C_1$-$C_4$alkoxy;

$R_6$-$R_{10}$ independently of one another represent hydrogen or a substituent selected from the group consisting of $C_1$-$C_4$alkyl, phenyl, phenyl-$C_1$-$C_4$alkyl, ($C_1$-$C_4$alkyl)$_{1-3}$phenyl and ($C_1$-$C_4$alkyl)$_{1-2}$hydroxyphenyl; and x represents a number between 1.0 and 2.0; and b) a polymer substrate.

2. A composition according to claim 1, wherein in the aminoguanidine phenylphosphinate salt (I)

$R_1$-$R_5$ represent hydrogen;

$R_6$-$R_{10}$ independently of one another represent hydrogen or $C_1$-$C_4$alkyl; and x represents a number between 1.0 and 2.0.

3. A composition according to claim 1, wherein in the aminoguanidine phenylphosphinate salt (I)

$R_1$-$R_5$ represent hydrogen;

$R_6$-$R_{10}$ represent hydrogen; and x represents a number between 1.0 and 2.0.

4. A composition according to claim 1, which comprises b) a polymer substrate selected from the group consisting of polyfunctional epoxide compounds and thermoplastic polymers.

5. A composition according to claim 4, which comprises b) at least one polyfunctional epoxide compound, wherein at least two epoxy groups of partial formula (A)

$$-\underset{R_1}{\overset{H}{\underset{|}{C}}}-(CH_2)_q-\underset{R_2}{\overset{|}{C}}\overset{O}{\diagdown}\underset{R_3}{\overset{|}{CH}} \tag{A}$$

are present, which are attached directly to carbon, oxygen, nitrogen or sulphur atoms, and wherein q represents zero, $R_1$ and $R_3$ both represent hydrogen and $R_2$ represents hydrogen or methyl; or wherein q represents zero or 1, $R_1$ and $R_3$ together form —CH$_2$—CH$_2$— or —CH$_2$—CH$_2$—CH$_2$— groups and $R_2$ represents hydrogen.

6. A composition according to claim 4, which comprises b) a polyfunctional epoxide compound and a hardener compound that contains at least two amino or two hydroxy groups.

7. A composition according to claim 1, which additionally comprises further additives selected from the group consisting of polymer stabilizers and additional flame retardants.

8. A composition according to claim 7, which comprises an additional flame retardant selected from the group consisting of melamine polyphosphate, ammonium polyphosphate, melamine ammonium phosphate, melamine ammonium polyphosphate, melamine ammonium pyrophosphate, a condensation product of melamine with phosphoric acid, other reaction products of melamine with phosphoric acid and mixtures thereof.

9. A composition according to claim 1, which comprises a further polymer substrate.

10. A process for imparting flame retardancy to a hardened polyfunctional epoxide composition, which process comprises adding to the composition an aminoguanidine phenylphosphinate salt (I)

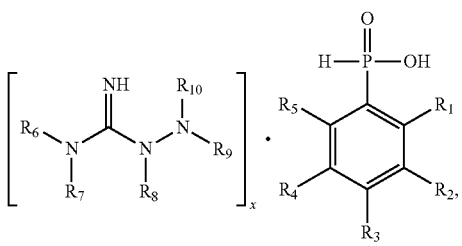

wherein
R$_1$-R$_5$ Independently of one another represent hydrogen or a substituent selected from the group consisting of C$_1$-C$_4$alkyl, hydroxy, hydroxy-C$_1$-C$_4$alkyl and C$_1$-C$_4$alkoxy;
R$_6$-R$_{10}$ independently of one another represent hydrogen or a substituent selected from the group consisting of C$_1$-C$_4$alkyl, phenyl, phenyl-C$_1$-C$_4$alkyl, (C$_1$-C$_4$alkyl)$_{1-3}$phenyl and (C$_1$-C$_4$alkyl)$_{1-2}$ hydroxyphenyl; and
x represents a number between 1.0 and 2.0.

11. An aminoauanidine ohenvlohosohinate salt of formula (I)

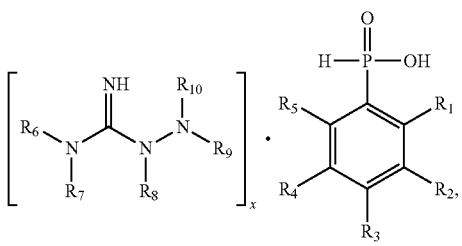

wherein
R$_1$-R$_5$ independently of one another represent hydrogen or a substituent selected from the group consisting of C$_1$-C$_4$alkyl, hydroxy, hydroxy-C$_1$-C$_4$alkyl and C$_1$-C$_4$alkoxy;
R$_6$-R$_{10}$ independently of one another represent hydrogen or a substituent selected from the group consisting of C$_1$-C$_4$alkyl, phenyl, phenyl-C$_1$-C$_4$alkyl, (C$_1$-C$_4$ alkyl)$_{1-3}$phenyl and (C$_1$-C$_4$alkyl)$_{1-2}$hydroxyphenyl; and
x represents a number between 1.0 and 2.0.

12. An aminoguanidine phenylphosphinate (I) according to claim 11, wherein
R$_1$-R$_5$ represent hydrogen;
R$_6$-R$_{10}$ independently of one another represent hydrogen or C$_1$-C$_4$alkyl; and
x represents a number between 1.0 and 2.0.

13. An aminoguanidine phenylphosphinate (I) according to claim 11, wherein
R$_1$-R$_5$ represent hydrogen;
R$_6$-R$_{10}$ independently of one another represent hydrogen; and
x represents a number between 1.0 and 2.0.

14. A composition according to claim 4, which comprises b) a polyfunctional epoxide compound and optionally a hardener compound.

15. A composition according to claim 4, which comprises b) a polyfunctional epoxide compound and a hardener compound.

16. A composition according to claim 4, which comprises b) a thermoplastic polymer.

* * * * *